United States Patent [19]

Cramp et al.

[11] Patent Number: 5,206,257
[45] Date of Patent: Apr. 27, 1993

[54] PESTICIDAL METHOD USING 2-PHENYLIMIDAZOLE DERIVATIVES

[75] Inventors: Susan M. Cramp; Leslie R. Hatton, both of Chelmsford, England

[73] Assignee: May & Baker Limited, Essex, England

[21] Appl. No.: 488,108

[22] Filed: Mar. 5, 1990

Related U.S. Application Data

[63] Continuation of Ser. No. 163,868, Mar. 3, 1988, abandoned.

[30] Foreign Application Priority Data

Mar. 5, 1987 [GB] United Kingdom ............ 8705183
Oct. 15, 1987 [GB] United Kingdom ............ 8724192

[51] Int. Cl.$^5$ .............................................. A01N 43/50
[52] U.S. Cl. ................................... 514/398; 514/396; 514/399; 514/400
[58] Field of Search ............... 514/400, 398, 396, 399

[56] References Cited

U.S. PATENT DOCUMENTS 3,772,319 11/1973 Heyes et al. .................. 260/309
4,314,844 2/1982 Swithenbank et al. ............ 71/92

FOREIGN PATENT DOCUMENTS 509058 4/1980 Australia .
50-125031 10/1975 Japan .
52-7434 1/1977 Japan .

OTHER PUBLICATIONS

Begland et al., *Journal of Organic Chemistry*, vol. 39, No. 16 (1974), pp. 2341-2350.
Kimoto et al., *Journal of Organic Chemistry*, vol. 47 (1982), pp. 2867-2872.

*Primary Examiner*—Allen J. Robinson
*Attorney, Agent, or Firm*—Burns, Doane, Swecker & Mathis

[57] ABSTRACT

The invention provides a method for the control of arthropod, plant nematode, helminth or protozoan pests using a 2-phenylimidazole derivative of the formula:

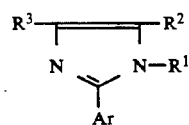

wherein
$R^1$ represents hydrogen, alkyl (optionally substituted by alkoxy, alkylthio, alkylsulphinyl, alkylsulphonyl, cyano, carboxy or alkoxycarbonyl), $R^2$ and $R^3$, each represents hydrogen, halogen, nitro, carboxy, cyano, alkoxycarbonyl, alkanoyl, or optionally alkyl substituted carbamoyl or sulphamoyl, or amino (optionally substituted by alkyl, alkoxycarbonyl or alkanoyl) or a group R, RO, RS, RSO or $RSO_2$ in which R represents alkyl (optionally substituted by halogen), and
Ar represents a group of the formula:

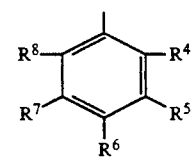

wherein $R^4$ and $R^6$ each represents halogen or a group R, RO, RS, RSO or $RSO_2$, and $R^5$, $R^7$ and $R^8$ each represents a substituent as defined for $R^4$ and $R^6$, or represents hydrogen, hydroxy, carboxy, nitro, cyano, amino, alkylamino (optionally substituted by alkyl, alkoxycarbonyl or alkanoyl), alkoxycarbonyl or alkanoyl or a pesticidally acceptable salt thereof, with the exclusion of compounds in which $R^2$ and $R^3$ simultaneously represent hydrogen atoms, compositions for use in the method and novel compounds of formula I.

5 Claims, No Drawings

PESTICIDAL METHOD USING 2-PHENYLIMIDAZOLE DERIVATIVES

This application is a continuation of application Ser. No. 07/163,868, filed Mar. 3, 1988, now abandoned.

This invention relates to the use of 2-phenylimidazole derivatives against arthropod, plant nematode, helminth and protozoan pests, to compositions containing them and to novel 2-phenylimidazole derivatives.

2-(2,4-Dichlorophenyl)-4,5-dicyanoimidazole is disclosed in Japanese patent publication no. 52-7434 (1977) as having herbicidal utility.

Japanese patent publication no. 50-125031 (1975) describes 4,5-dicyanoimidazole and 2-alkyl-4,5-dicyanoimidazoles as having acaricidal, herbicidal and insecticidal utility.

British Patent No. 1399291 describes 4-nitroimidazoles which are stated to possess anticoccidial activity or to be useful in the preparation of compounds possessing such activity. The compounds are described as carrying on the 2- position of the imidazole ring a wide range of substituents including substituted phenyl. There is, however, no disclosure of any compound carrying on the 2- position a 2,4-disubstituted phenyl group, nor is there any disclosure or suggestion that the compounds might possess any activity other than anticoccidial activity.

It has now unexpectedly been found after extensive research and experimentation that the 2-phenylimidazole derivatives of the general formula I depicted hereinafter wherein $R^1$ represents the hydrogen atom or a straight-or branched-chain alkyl group containing from 1 to 6 carbon atoms which is optionally substituted by a straight- or branched-chain alkoxy, alkylthio, alkylsulphinyl or alkylsulphonyl group containing from 1 to 6 carbon atoms, or by a cyano or carboxy group or by a straight- or branched-chain alkoxycarbonyl group containing from 2 to 7 carbon atoms, $R^2$ and $R^3$, which may be the same or different, each represents a hydrogen or halogen (i.e. fluorine, chlorine, bromine or iodine) atom, a nitro, carboxy or cyano group, a straight- or branched- chain alkoxycarbonyl or alkanoyl group containing from 2 to 7 carbon atoms, a carbamoyl or sulphamoyl group which may be substituted by one or two straight- or branched-chain alkyl groups each containing from 1 to 6 carbon atoms, an amino group which may be substituted on the nitrogen atom by one or two substituents chosen from straight- or branched-chain alkyl groups containing from 1 to 6 carbon atoms and straight- or branched- chain alkoxycarbonyl and alkanoyl groups containing from 2 to 7 carbon atoms, or represents a group R, RO, RS, RSO or $RSO_2$ in which R represents a straight- or branched-chain alkyl group containing from 1 to 6 carbon atoms which is optionally substituted by one or more halogen atoms, and Ar represents an optionally substituted 2,4-disubstituted phenyl group of the general formula II wherein $R^4$ and $R^6$, which may be the same or different, each represents a halogen (i.e. fluorine, chlorine, bromine or iodine) atom or a group R, RO, RS, RSO or $RSO_2$ in which R represents a straight- or branched-chain alkyl group containing from 1 to 6 carbon atoms which is optionally substituted by one or more halogen atoms, and $R^5$, $R^7$ and $R^8$, which may be the same or different, each represents a substituent as defined above for $R^4$ and $R^6$, or represents a hydrogen atom, a hydroxy, carboxy, nitro, cyano or amino group, a straight- or branched-chain alkylamino group containing from 1 to 6 carbon atoms which may be substituted on the nitrogen atom by a straight- or branched-chain alkyl group containing from 1 to 6 carbon atoms or by a straight- or branched- chain alkoxycarbonyl or alkanoyl group containing from 2 to 7 carbon atoms or represents a straight- or branched-chain alkoxycarbonyl or alkanoyl group containing from 2 to 7 carbon atoms, and their pesticidally acceptable salts, with the exclusion of compounds in which $R^2$ and $R^3$ simultaneously represent hydrogen atoms have valuable activity against arthropod, plant nematode, helminth and protozoan pests.

The person skilled in the art will perceive that certain of the compounds of general formula I, for example those containing amino groups, will tend to have basic properties whilst certain of the compounds, for example those containing carboxy groups, will tend to have acidic properties. Pesticidally acceptable salts formed by such compounds with acids or bases, respectively, are included in the scope of general formula I and are meant to be referred to when reference is made to compounds of general formula I, whenever the context so permits.

By the term "pesticidally acceptable salts" as used in this specification is meant salts of acids or of bases which are known and accepted in the art for the formulations of salts of biologically active compounds for agricultural or horticultural use. When intended for application to vertebrates to combat infection or infestation by arthropods, helminths or protozoa, the salts used will be non-toxic. By the term 'non-toxic' is meant salts with acids/bases the anions/cations of which are innocuous to the vertebrates at the doses administered and which do not vitiate the beneficial effects produced by the cation/anion. Suitable salts of acids include salts of inorganic acids such as hydrochlorides, sulphates, phosphates and nitrates and salts of organic acids, for example acetates. Suitable salts of bases include alkali metal, e.g. sodium or potassium, salts, alkaline earth metal, e.g. calcium or magnesium, salts and salts of ammonia or of organic bases, e.g. amines (e.g. diethanolamine or triethanolamine).

Furthermore, it will be understood by those skilled in the art that the compounds of general formula I wherein $R^1$ represents the hydrogen atom exhibit tautomerism such that the hydrogen atom may reside on either of the imidazole ring nitrogen atoms, and that the forms thus described may be present to a greater or lesser degree and are in a state of dynamic equilibrium with each other. Furthermore, in certain cases the substituents $R^1$, $R^2$, $R^3$, $R^4$, $R^5$, $R^6$, $R^7$ and $R^8$ contribute to optical and/or stereoisomerism. All such forms are embraced by the present invention.

Preferred classes of compounds of general formula I include those wherein one or more of the symbols $R^1$, $R^2$, $R^3$ and Ar is as defined below, the other symbols $R^1$, $R^2$, $R^3$ and Ar being as hereinbefore defined:

(i) $R^1$ represents the hydrogen atom;
(ii) $R^2$ and $R^3$ are both other than hydrogen atoms;
(iii) Ar represents a 2-$R^4$-4-$R^6$-substituted phenyl group optionally bearing a substituent which may be the same or different selected from halogen atoms (especially chlorine, bromine or fluorine atoms), R, RO, RS, RSO or $RSO_2$, especially when Ar represents a phenyl group bearing such a substituent in the 6-position, more especially when Ar represents the 2,6- dichloro-4-trifluoromethylphenyl, 2,6-dichloro-4-trifluoromethoxyphenyl or 2-chloro-4-trifluoromethylphenyl group;

(iv) $R^2$ represents a halogen (preferably the bromine) atom, or a nitro, cyano, trifluoromethyl or alkyl group or represents a group RO, RS, RSO or $RSO_2$ in which R represents a straight- or branched-chain alkyl group containing from 1 to 6 carbon atoms which is optionally substituted by one or more halogen atoms;

(v) $R^3$ represents a halogen (preferably the bromine) atom, or a nitro, cyano, trifluoromethyl or alkyl group;

(vi) $R^4$ represents a halogen (preferably the chlorine) atom and (vii) $R^6$ represents a group R, RO, RS, RSO or $RSO_2$ in which R represents a straight- or branched-chain alkyl group containing from 1 to 6 carbon atoms which is substituted by one or more halogen atoms (preferably $R^6$ represents the trifluoromethyl group).

Compounds of general formula I in which $R^8$ represents a halogen (preferably the chlorine) atom are also preferred.

A preferred class of compounds of general formula I is where $R^1$ represents the hydrogen atom, $R^2$ and $R^3$, which may be the same or different, each represents a hydrogen or halogen (preferably the bromine) atom, a nitro, carboxy or cyano group, a straight- or branched-chain alkoxycarbonyl group containing from 2 to 7 carbon atoms, a carbamoyl or sulphamoyl group which may be substituted by one or two straight- or branched-chain alkyl groups each containing from 1 to 6 carbon atoms, an amino group which may be substituted on the nitrogen atom by one or two substitutents chosen from straight- or branched-chain alkyl groups containing from 1 to 6 carbon atoms and straight- or branched-chain alkoxycarbonyl and alkanoyl groups containing from 2 to 7 carbon atoms, or represents a straight- or branched-chain alkyl or alkylthio group containing from 1 to 6 carbon atoms which is optionally substituted by one or more halogen atoms, and $R^4$ represents a halogen (preferably the chlorine) atom, $R^6$ represents a halogen (preferably the chlorine) alkoxy or alkylthio group containing from 1 to 6 carbon atoms which is substituted by one or more halogen atoms, $R^5$ and $R^7$ represent hydrogen atoms and $R^8$ represents a hydrogen or halogen (preferably the chlorine) atom.

An especially preferred class of compounds of general formula I is where $R^1$ represents the hydrogen atom, $R^2$ represents a trifluoromethyl or trifluoromethoxy group or a methylthio, methylsulphinyl or methylsulphonyl group which is substituted by one, two or three fluorine atoms and $R^3$ represents a halogen (preferably the bromine) atom, or a nitro or cyano group.

Compounds of general formula I which are particularly important are the following:

B—2-(2,6-dichloro-4-trifluoromethoxyphenyl)-4,5-dicyanoimidazole

C—2-(2-chloro-4-trifluoromethylphenyl)-4,5-dicyanoimidazole

D—2-(2,6-dichloro-4-trifluoromethylphenyl)-4-trifluoromethylimidazole

E—5-bromo-2-(2,6-dichloro-4-trifluoromethylphenyl)-4-trifluoromethylimidazole

F—2-(2,6-dichloro-4-trifluoromethylphenyl)-5-nitro-4-trifluoromethylimidazole

G—5-cyano-2-(2,6-dichloro-4-trifluoromethylphenyl)-imidazole-4-carboxylic acid

H—5-cyano-2-(2,6-dichloro-4-trifluoromethylphenyl)imidazole

I—4-bromo-5-cyano-2-(2,6-dichloro-4-trifluoromethylphenyl)imidazole

J—5-cyano-2-(2,6-dichloro-4-trifluoromethylphenyl)imidazole-4-carboxamide

K—5-cyano-2-(2,6-dichloro-4-trifluoromethoxyphenyl)imidazole-4-carboxamide

L—ethyl 5-cyano-2-(2,6-dichloro-4-trifluoromethylphenyl)imidazole-4-carboxylate

M—2-(2,6-dichloro-4-trifluoromethylphenyl)imidazole-4,5-dicarboxamide

N—2-(2,6-dichloro-4-trifluoromethylphenyl)-4,5-dimethylimidazole

O—2-(2,6-dichloro-4-trifluoromethylphenyl)-4-methylimidazole

P—2-(2,6-dichloro-4-trifluoromethylphenyl)-4-methyl-5-nitroimidazole

Q—2-(2,6-dichloro-4-trifluoromethylphenyl)-4-methylimidazole-5-sulphonamide

R—2-(2,6-dichloro-4-trifluoromethylphenyl)-4-methyl-5-methylthioimidazole

S—2-(2,6-dichloro-4-trifluoromethylphenyl)-4-nitroimidazole

T—4,5-dibromo-2-(2,6-dichloro-4-trifluoromethylphenyl)imidazole

U—4-bromo-2-(2,6-dichloro-4-trifluoromethylphenyl)imidazole

V—4-bromo-2-(2,6-dichloro-4-trifluoromethylphenyl)-5-nitroimidazole

W—2-(2-bromo-4-trifluoromethylphenyl)-4,5-dicyanoimidazole

X—N,N-diethyl 2-(2,6-dichloro-4-trifluoromethylphenyl)-5-cyanoimidazole-4-carboxamide Y—2-(2,3,5,6-tetrachloro-4-trifluoromethylthiophenyl)-4,5-dicyanoimidazole Z—4-amino-5-cyano-2-(2,4-dichlorophenyl)imidazole AA—N,N-diethyl 2-(2,4-dichlorophenyl)-5-trifluoromethylimidazole-4-carboxamide BB—4-(tert.butoxycarbonylamino)-5-cyano-2-(2,4-dichlorophenyl)imidazole CC—5-cyano-2-(2,4-dichlorophenyl)imidazole-4-carboxylic acid DD—2-(2,4-dichlorophenyl)imidazole-4,5-dicarboxylic acid The letters A to DD are assigned to the above compounds for identification and reference hereinafter.

Especially preferred compounds of general formula I are: A, B, E, F, T and V.

According to a feature of the present invention, there is provided a method for the control of arthropod, plant nematode, helminth or protozoan pests at a locus which comprises the treatment of the locus (e.g. by application or administration) with an effective amount of a compound of general formula I, or a pesticidally acceptable salt thereof, wherein the various symbols are as hereinbefore defined. The compounds of general formula I may, in particular, be used in the fields of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fishes, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata*) and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,); Diptera (e.g. Aedes spp., Anopheles spp., Musca spp., Hypoderma spp., Gasterophilus spp., Simulium spp.); Hemiptera (e.g. Triatoma spp.); Phthiraptera (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); against infections of the gastro-intestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus battus, Ostertagia circumcincta, Trichostrongylus axei*, Cooperia spp. and *Hymenolepis nana*; in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoma cruzi*, Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal feedstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and similar arthropod pests in infested domestic and industrial premises and in the control of mosquito larvae in waterways, wells, reservoirs or other running or standing water; for the treatment of foundations, structure and soil in the prevention of the attack on buildings by termites, for example, Reticulitermes spp., Heterotermes spp., Coptotermes spp.; in agriculture, against adults, larvae and eggs of Lepidoptera (butterflies and moths), e.g. Heliothis spp. such as *Heliothis virescens* (tobacco budworm), *Heliothis armigera* and *Heliothis zea*, Spodoptera spp. such as *S. exempta, S. littoralis* (Egyptian cotton worm), *S. eridania* (southern army worm), *Mamestra configurata* (bertha army worm); Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond back moth); against adults and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Meligethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Psuedococcus spp., Helopeltis spp. (mosquito bugs), Lygus spp., Dysdercus spp., Oxycarenus spp., Nezara spp.; Hymenoptera e.g. Athalia spp. and Cephus spp. (saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci*; Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphagotarsonemus spp.; Blaniulus spp. (millipedes), Scutigerella spp. (symphilids), Oniscus spp. (woodlice) and Triops spp. (crustacea); nematodes which attack plants and trees of importance to agriculture, forestry, horticulture either directly or by spreading bacterial, viral, mycoplasma or fungal diseases of the plants, rootknot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *multicinctus*); Hemicycliophora spp. (e.g. *H. gracilis*-Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

The invention also provides a method for the control of arthropod or nematode pests of plants which comprises the application to the plants or to the medium in which they grow of an effective amount of a compound of general formula I or a pesticidally acceptable salt thereof.

For the control of arthropods and nematodes, the active compound is generally applied to the locus in which arthropod or nematode infestation is to be controlled at a rate of about 0.1 kg to about 25 active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of general formula I may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

The compounds of general formula I are of value in controlling pests which feed on parts of the plant remote from the point of application, e.g. leaf feeding insects are killed by the subject compounds applied to roots.

In addition the compounds may reduce attacks on the plant by means of antifeeding or repellant effects.

The compounds of general formula I are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus), beetles (e.g. scolytids, platypodids, lyctids, bostrychids, cerambycids, anobiids) or termites, for example, Reticulitermes spp., Heterotermes spp., Coptotermes spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula I are of particular value in the control of arthropods, helminths or protozoa which are injurious to, or spread or act as vectors of diseases in man and domestic animals, for example those hereinbefore mentioned, and more especially in the control of ticks, mites, lice, fleas, midges and biting, nuisance and myiasis flies. The compounds of general formula I are particularly useful in controlling arthropods, helminths or protozoa which are present inside domestic host animals or which feed in or on the skin or suck the blood of the animal, for which purpose they may be administered orally, parenterally, percutaneously or topically.

Coccidiosis, a disease caused by infections by protozoan parasites of the genus Eimeria, is an important potential cause of economic loss in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection.

Administration of a small amount of a compound of general formula I or a pesticidally acceptable salt thereof preferably by combination with poultry feed is effective in preventing or greatly reducing the incidence of coccidiosis. The compounds are effective against both the cecal form (caused by $E.$ $tenella$) and the intestinal forms (principally caused by $E.$ $acervulina$, $E.$ $brunetti$, $E.$ $maxima$ and $E.$ $necatrix$).

The compounds of general formula I also exert an inhibitory effect on the oocysts by greatly reducing the number and or the sporulation of those produced.

The compositions hereinafter described for topical application to man and animals and in the protection of stored products, household goods, property and areas of the general environment may, in general, alternatively be employed for application to growing crops and crop growing loci and as a seed dressing.

Suitable means of applying the compounds of general formula I include:

to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, waxsmears and livestock self-treatment systems;

to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their faeces;

to growing crops as foliar sprays, dusts, granules, fogs and foams; also as suspensions of finely divided and encapsulated compounds of general I; as soil and root treatments by liquid drenches, dusts, granules, smokes and foams; and as seed dressings by liquid slurries and dusts.

The compounds of general formula I may be applied to control arthropods, helminths or protozoa in compositions of any type known to the art suitable for internal or external administration to vertebrates or application for the control of arthropods in any premises or indoor or outdoor area, containing as active ingredient at least one compound of general formula I in association with one or more compatible diluents or adjuvants appropriate for the intended use. All such compositions may be prepared in any manner known to the art.

Compositions suitable for administration to vertebrates or man include preparations suitable for oral, parenteral, percutaneous, e.g. pour-on, or topical administration.

Compositions for oral administration comprise one or more of the compounds of general formula I in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Solid or liquid baits suitable for controlling arthropods comprise one or more compounds of general formula I and a carrier or diluent which may include a food substance or some other substance to induce consumption by the arthropod.

Liquid compositions include water miscible concentrates, emulsifiable concentrates, flowable suspensions, wettable or soluble powders containing one or more compounds of general formula I which may be used to treat substrates or sites infested or liable to infestation by arthropods including premises, outdoor or indoor storage or processing areas, containers or equipment and standing or running water.

Solid homogenous or heterogenous compositions containing one or more compounds of general formula I, for example granules, pellets, briquettes or capsules, may be used to treat standing or running water over a period of time. A similar effect may be achieved using trickle or intermittent feeds of water dispersible concentrates as described herein.

Compositions in the form of aerosols and aqueous or non-aqueous solution or dispersions suitable for spraying, fogging and low- or ultra-low volume spraying may also be used.

Suitable solid diluents which may be used in the preparation of compositions suitable for applying the compounds of general formula I include aluminium silicate, kieselguhr, corn husks, tricalcium phosphate, powdered cork, adsorbent carbon black, magnesium silicate, a clay such as kaolin, bentonite or attapulgite, and water soluble polymers and such solid compositions may, if desired, contain one or more compatible wetting, dispersing, emulsifying or colouring agents which, when solid, may also serve as diluent.

Such solid compositions, which may take the form of dusts, granules or wettable powders, are generally prepared by impregnating the solid diluents with solutions of the compound of general formula I in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g. gelatin, synthetic resins and polyamides.

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octyl-phenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of general formula I may take the form of solutions, suspensions and emulsions of the compounds of general formula I optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of general formula I may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of general formula I which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellants or pheromones, reodorants, flavouring agents, dyes and auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjuntion with, the compositions of the present invention are: acephate, chlorpyrifos, demeton-S-methyl, disulfoton, ethoprofos, fenitrothion, malathion, monocrotophos, parathion, phosalone, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine and dimetridazole.

The compositions for application to control arthropod, plant nematode, helminth or protozoan pests usually contain from 0.00001% to 95%, more particularly from 0.0005% to 50%, by weight of one or more compounds of general formula I or of total active ingredients (that is to say the compound(s) of general formula I together with other substances toxic to arthropods and plant nematodes, anthelmintics, anticoccidials, synergists, trace elements or stabilisers). The actual compositions employed and their rate of application will be selected to achieve the desired effect(s) by the farmer, livestock producer, medical or veterinary practitioner, pest control operator or other person skilled in the art. Solid and liquid compositions for application topically to animals, timber, stored products or household goods usually contain from 0.00005% to 90%, more particularly from 0.001% to 10%, by weight of one or more compounds of general formula I. For administration to animals orally or parenterally, including percutaneously solid and liquid compositions normally contain from 0.1% to 90% by weight of one or more compound of general formula I. Medicated feedstuffs normally contain from 0.001% to 3% by weight of one or more compounds of general formula I. Concentrates and supplements for mixing with feedstuffs normally contain from 5% to 90%, and preferably from 5% to 50%, by weight of one or more compounds of general formula I. Mineral salt licks normally contain from 0.1% to 10% by weight of one or more compounds of general formula I.

Dusts and liquid compositions for application to livestock, persons, goods, premises or outdoor areas may contain 0.0001% to 15%, and more especially 0.005% to 2.0%, by weight of one or more compounds of general formula I. Suitable concentrations in treated waters are between 0.0001 ppm and 20 ppm, and more especially 0.001 ppm to 5.0 ppm, of one or more compounds of general formula I and may also be used therapeutically in fish farming with appropriate exposure times. Edible baits may contain from 0.01% to 5% and preferably 0.01% to 1.0%, by weight of one or more compounds of general formula I.

When administered to vertebrates parenterally, orally or by percutaneous or other means, the dosage of compounds of general formula I will depend upon the species, age and health of the vertebrate and upon the nature and degree of its actual or potential infestation by arthropod, helminth or protozoan pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parenteral administration. By use of sustained release formulations or devices, the daily doses required over a period of months may be combined and administered to animals on a single occasion.

The following Composition Examples illustrate compositions for use against arthropod, plant nematode, helminth or protozoan pests which comprise, as active ingredient, compounds of general formula I. The compositions described in Composition Examples 1 to 6 can each be diluted in water to give a sprayable composition at concentrations suitable for use in the field.

COMPOSITION EXAMPLE 1

A water soluble concentrate was prepared from

| | |
|---|---|
| 2-(2,6-dichloro-4-trifluoromethyl-phenyl)-4,5-dicyanoimidazole | 7% w/v |
| Ethylan BCP | 10% w/v |
| and N-methylpyrrolidone | to 100% by volume | by dissolving the Ethylan BCP in a portion of N-methylpyrrolidone, and then adding the active ingredient with heating and stirring until dissolved. The resulting solution was made up to volume by adding the remainder of the solvent.

COMPOSITION EXAMPLE 2

An emulsifiable concentrate was prepared from

| | |
|---|---|
| 2-(2,6-dichloro-4-trifluoromethyl-phenyl)-4,5-dicyanoimidazole | 7% w/v |
| Soprophor BSU | 4% w/v |
| Arylan CA | 4% w/v |
| N-methylpyrrolidone | 50% w/v |
| and Solvesso 150 | to 100% by volume | by dissolving Soprophor BSU, Arylan CA and the active ingredient in N-methylpyrrolidone, and then adding Solvesso 150 to volume.

COMPOSITION EXAMPLE 3

A wettable powder was prepared from

| | |
|---|---|
| 2-(2,6-dichloro-4-trifluoromethyl-phenyl)-4,5-dicyanoimidazole | 40% w/v |
| Arylan S | 2% w/v |
| Darvan No. 2 | 5% w/v |
| and Celite PF | to 100% by weight | by mixing the ingredients, and grinding the mixture in a hammer-mill to a particle size less than 50 microns.

COMPOSITION EXAMPLE 4

An aqueous flowable formulation was prepared from

| | |
|---|---|
| 2-(2,6-dichloro-4-trifluoromethyl-phenyl)-4,5-dicyanoimidazole | 30% w/v |
| Ethylan BCP | 1% w/v |
| Sopropon T36 | 0.2% w/v |
| Ethylene glycol | 5% w/v |
| Rhodigel 23 | 0.15% w/v |
| and Water | to 100% by volume | by intimately mixing the ingredients and grinding in a bead mill until the median particle size was less than 3 microns.

COMPOSITION EXAMPLE 5

An emulsifiable suspension concentrate was prepared from

| | |
|---|---|
| 2-(2,6-dichloro-4-trifluoromethyl-phenyl)-4,5-dicyanoimidazole | 30% w/v |
| Ethylan BCP | 10% w/v |
| Bentone 38 | 0.5% w/v |
| and Solvesso 150 | to 100% by volume | by intimately mixing the ingredients and grinding in a bead mill until the median particle size was less than 3 microns.

COMPOSITION EXAMPLE 6

Water dispersible granules were prepared from

| | |
|---|---|
| 2-(2,6-dichloro-4-trifluoromethyl-phenyl)-4,5-dicyanoimidazole | 30% w/v |
| Darvan No. 2 | 15% w/v |
| Arylan S | 8% w/v |
| and Celite PF | to 100% by weight | by mixing the ingredients, micronising in a fluid-energy mill, and then granulating in a rotating pelletiser by spraying on sufficient water (up to 10% w/w). The resulting granules were dried in a fluid-bed drier to remove excess water.

Descriptions of commercial ingredients used in the foregoing Composition Examples

| | |
|---|---|
| Ethylan BCP | nonylphenol ethylene oxide condensate |
| Soprophor BSU | condensate of tristyrylphenol and ethylene oxide |
| Arylan CA | 70% w/v solution of calcium dodecylbenzenesulphonate |
| Solvesso 150 | light $C_{10}$-aromatic solvent |
| Arylan S | sodium dodecylbenzenesulphonate |
| Darvan | sodium lignosulphonate |
| Celite PF | synthetic magnesium silicate carrier |
| Sopropon T36 | sodium salt of polycarboxylic acid |
| Rhodigel 23 | polysaccharide xanthan gum |
| Bentone 38 | organic derivative of magnesium montmorillonite |

COMPOSITION EXAMPLE 7

A dusting powder may be prepared by intimately mixing:

| | |
|---|---|
| 2-(2,6-dichloro-4-trifluoromethyl-phenyl)-4,5-dicyanoimidazole | 1 to 10% w/w (weight/weight) |
| Talc superfine | to 100% by weight |

This powder may be applied to a locus of arthropod infestation, for example refuse tips or dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

COMPOSITION EXAMPLE 8

An edible bait may be prepared by intimately mixing:

| | |
|---|---|
| 2-(2,6-dichloro-4-trifluoromethyl-phenyl)-4,5-dicyanoimidazole | 0.1 to 1.0% w/w |
| Wheat flour | 80% w/w |
| Molasses | to 100% w/w |

This edible bait may be distributed at a locus, for example domestic and industrial premises, e.g. kitchens, hospitals or stores, or outdoor areas, infested by arthropods, for example ants, locusts, cockroaches and flies, to control the arthropods by oral ingestion.

COMPOSITION EXAMPLE 9

A solution may be prepared containing:

| | |
|---|---|
| 2-(2,6-dichloro-4-trifluoromethyl-phenyl)-4,5-dicyanoimidazole | 15% w/v (weight/volume) |
| Dimethylsulphoxide | to 100% by volume | by dissolving the imidazole derivative in a portion of the dimethylsulphoxide and then adding more dimethylsulphoxide to the desired volume. This solution may be applied to domestic animals infested by arthropods, percutaneously as a pour-on application or, after sterilisation by filtration through a polytetrafluoroethylene membrane (0.22 μm pore size), by parenteral injection, at a rate of application of from 1.2 to 12 ml of solution per 100 kg of animal body weight.

COMPOSITION EXAMPLE 10

A wettable powder may be formed from:

| | |
|---|---|
| 2-(2,6-dichloro-4-trifluoromethyl-phenyl)-4,5-dicyanoimidazole | 50% w/w |
| Ethylan BCP (a nonylphenol/ethylene oxide condensate containing 9 moles of ethylene oxide per mol of phenol) | 5% w/w |
| Aerosil (silicon dioxide of microfine-particle size) | 5% w/w |
| Celite PF (synthetic magnesium silicate carrier) | 40% w/w | by adsorbing the Ethylan BCP onto the Aerosil, mixing with the other ingredients and grinding the mixture in a hammer-mill to give a wettable powder, which may be diluted with water to a concentration of from 0.001% to 2% w/v of the imidazole compound and applied to a locus of infestation by arthropods, for example dipterous larvae, or plant nematodes by spraying, or to domestic animals infested by, or at risk of infestation by, arthropods, helminths or protozoa, by spraying or dipping, or by oral administration as drinking water, to control the arthropods, helminths or protozoa.

COMPOSITION EXAMPLE 11

A slow release bolus may be formed from granules containing a density agent, binder, slow-release agent and 2-(2,6-dichloro-4-trifluoromethylphenyl)-4,5-dicyanoimidazole compound at varying percentage compositions. By compressing the mixture a bolus with a specific gravity of 2 or more can be formed and may be administered orally to ruminant domestic animals for retention within the reticulo-rumen to give a continual slow release of imidazole compound over an extended period of time to control infestation of the ruminant domestic animals by arthropods, helminths or protozoa.

COMPOSITION EXAMPLE 12

A slow release composition may be prepared from:

| | |
|---|---|
| 2-(2,6-dichloro-4-trifluoromethyl-phenyl)-4,5-dicyanoimidazole | 0.5 to 25% w/w |
| polyvinylchloride base | to 100% w/w | by blending the polyvinylchloride base with the imidazole compound and a suitable plasticiser, e.g. dioctyl phthalate, and melt-extruding or hot-moulding the homogenous composition into suitable shapes, e.g. granules, pellets, brickettes or strips, suitable, for example, for addition to standing water or, in the case of strips, fabrication into collars or ear-tags for attachment to domestic animals, to control insect pests by slow release of the imidazole compound.

Similar compositions may be prepared by replacing the 2-(2,6-dichloro-4-trifluoromethylphenyl)-4,5-dicyanoimidazole in the Composition Examples by the appropriate quantity of any other compound of general formula I.

The compounds of general formula I may be prepared by the application or adaptation of known methods that is to say methods heretofore used or known in the literature.

Compounds of general formula I wherein $R^1$ represents the hydrogen atom may be reacted with the appropriate alkyl halide, i.e. chloride, bromide or iodide, in the presence of a base to give the corresponding N-alkylated compounds of general formula I wherein $R^1$ represents an optionally substituted alkyl group as hereinbefore defined.

According to a feature of the present invention, compounds of general formula I wherein $R^1$ represents the hydrogen atom, $R^2$ represents a cyano or optionally substituted carbamoyl group as hereinbefore defined, $R^3$ represents the cyano group and Ar is as hereinbefore defined, i.e. compounds of general formula III wherein $R^9$ represents a cyano or optionally substituted carbamoyl group as hereinbefore defined and Ar is as hereinbefore defined, within the scope of general formula I, may be prepared by the oxidative cyclisation of a compound of general formula IV wherein $R^9$ and Ar are as hereinbefore defined, for example in the presence of a quinone, for example 2,3-dichloro-5,6-dicyano-1,4-benzoquinone, in an inert organic solvent, e.g. acetonitrile, at elevated temperature, e.g. at the reflux temperature of the reaction mixture; or chlorine, bromine or iodine, optionally in the presence of a buffering agent, e.g. sodium acetate, in an inert organic solvent, e.g. dichloromethane, N-methyl-2-pyrrolidone or dimethylformamide at a temperature from room temperature to the reflux temperature of the reaction mixture; or N-chlorosuccinimide in the presence of a base, e.g. triethylamine, in an inert organic solvent.

Other representative methods of forming the substituted heterocycle include the reaction of the corresponding benzaldehyde with tartaric acid dinitrate in the presence of ammonium hydroxide (affording compounds of general formula I wherein $R^1$=H, $R^2$ and $R^3$=carboxy), with cyanogen in the presence of hydrogen chloride (affording compounds of general formula I wherein $R^1$=H, $R^2$ and $R^3$=chloro), with an α-ketoaldehyde (optionally prepared in situ from a dibromomethyl alkyl ketone and sodium acetate) in the presence of ammonia (affording compounds of general formula I wherein $R^1$=H, $R^2$=optionally substituted alkyl, $R^3$=H) or with dialkyl glyoxal in the presence of ammonium acetate (affording compounds of general formula I wherein $R^1$=H, $R^2$ and $R^3$=optionally substituted alkyl); or the reaction of a compound of general formula V with bromomethyl alkyl ketone in the presence of potassium carbonate and dimethylformamide or alkali metal alkoxide and alkanol (affording compounds of general formula I wherein $R^2$=alkanoyl, $R^3$=amino), or the reaction of a compound of general formula VI with (optionally substituted amino)acetonitrile hydrochloride in the presence of triethylamine or alkali metal alkoxide in alkanol (affording compounds of general formula I wherein $R^2$=cyano, $R^3$=amino)

or the reaction of a compound of general formula VII with 1-(optionally substituted alkyl)2-trimethylsilyloxyethylene in the presence of pyridine in chloroform (affording compounds of general formula I wherein $R^2$=optionally substituted alkyl, $R^3$=H)

or the reaction of a compound of general formula VIII with ammonium acetate and acetic acid (affording compounds of general formula I wherein $R^1$=H, $R^2$ and $R^3$=optionally substituted alkyl).

Interconversions of compounds of general formula I are possible, by the application or adaptation of known methods, for example:

(i) compounds of general formula I wherein respectively either $R^2$ represents a carbamoyl group and $R^3$ represents a cyano group (or $R^2$ represents a cyano group and $R^3$ represents a carbamoyl group), or $R^2$ and $R^3$ both represent carbamoyl groups, $R^1$ represents the hydrogen atom and Ar is as hereinbefore defined may be prepared from compounds of general formula III wherein $R^9$ represents the cyano group and Ar is as hereinbefore defined by hydrolysis, for example in the presence of an alkali metal hydroxide, e.g. sodium hydroxide, at temperatures between 15° C. and 100° C., or in the presence of an alkali metal hydroxide, e.g. potassium hydroxide, in ethanol at reflux, respectively (ii) compounds containing amino group(s) can be prepared by the reduction of compounds containing nitro group(s) for example by catalytic hydrogenation in the presence of 5% palladium on carbon;

(iii) compounds containing amino group(s) can be prepared by reaction of unsubstituted compounds with hydroxylamine;

(iv) compounds containing carboxy group(s) can be prepared by the hydrolysis of compounds containing alkoxycarbonyl group(s) for example using an aqueous solution of an alkali metal hydroxide;

(v) compounds containing alkoxycarbonyl group(s) can be prepared by the esterification of compounds containing carboxy group(s) or by the transesterification of compounds containing other alkoxycarbonyl group(s) for example by heating with the appropriate alcohol at the reflux temperature of the reaction mixture in the presence of an acid catalyst such as concentrated sulphuric acid;

(vi) compounds containing nitro group(s) can be prepared by nitration of unsubstituted compounds by heating with a mixture of nitric and sulphuric acids at a temperature from 70° C. to 120° C.;

(vii) compounds containing alkoxycarbonyl group(s) can be prepared by solvolysis e.g.hydrolysis of compounds containing cyano group(s) in the presence of an acid catalyst such as concentrated hydrochloric acid;

(viii) compounds containing carboxy group(s) can be decarboxylated for example by heating at a temperature from 150° C. to 250° C. in an inert organic solvent such as diethylene glycol;

(ix) compounds containing halogen atom(s) can be prepared by halogenation of unsubstituted compounds in an organic solvent such as chloroform or acetic acid optionally in the presence of a buffering agent such as sodium acetate at a temperature from room temperature to the reflux temperature of the reaction mixture;

(x) compounds containing chlorine, bromine or iodine atoms can be prepared by diazotisation of compounds containing amino groups followed by for example reaction with aqueous hydrochloric or hydrobromic acid in the presence of cuprous chloride or cuprous bromide or with potassium iodide in sulphuric acid;

(xi) compounds containing alkylthio group(s) can be prepared by reaction of compounds containing halogen atom(s) with thiol derivatives in an inert organic solvent such as dimethylformamide or by alkylation of thiols (prepared from halogen containing compounds by for example reaction with hydrogen sulphide in the presence of base such as pyridine or with sodium hydrosulphide in an organic solvent);

(xii) compounds containing alkylthio group(s) can be prepared by reaction of unsubstituted compounds with (optionally halogen substituted) alkylsulphenyl halides optionally in the presence of an organic base or Lewis acid catalyst at a temperature from 0° C. to 80° C. under increased pressure as necessary;

(xiii) compounds containing alkylthio group(s) can be prepared by chlorosulphonation of unsubstituted compounds using chlorosulphonic acid at elevated temperatures, followed by reduction of corresponding sulphonyl chlorides using for example stannous chloride in hydrochloric acid, followed by alkylation using alkyl halide in the presence of a base such as an alkali metal hydroxide;

(xiv) compounds containing alkylsulphinyl or alkylsulphonyl group(s) can be prepared by oxidation of compounds containing alkylthio group(s) using an oxidising agent such as hydrogen peroxide or an organic peracid such as m-chloroperbenzoic acid;

(xv) compounds containing carbamoyl group(s) can be rearranged to carbamates for example using a halogen such as chlorine or bromine in the presence of aqueous alkali metal hydroxide solution at a temperature from 50° C. to 100° C.;

(xvi) compounds containing sulphamoyl group(s) can be prepared by chlorosulphonation of unsubstituted compounds using chlorosulphonic acid at elevated temperatures, followed by reaction of corresponding sulphonyl chlorides with ammonia or an amine in aqueous or aqueous-alcoholic medium;

(xvii) compounds containing carbamoyl group(s) can be prepared from compounds containing carboxy group(s) by conversion to the corresponding acid halide for example by reacting with thionyl chloride or diethylaminosulphur trifluoride at a temperature from 0° C. to the reflux temperature of the reaction mixture, followed by reacting the acid halide with ammonia or an amine in an inert organic solvent such as dichloromethane;

(xviii) compounds containing amino group(s) can be prepared from compounds containing carboxy group(s) for example by reacting with diphenylphosphoryl azide in the presence of an alcohol e.g. 2-methylpropan-2-ol and a base such as triethylamine at the reflux temperature of the reaction mixture, followed by decomposing the carbamate of formula I obtained, for example with iodotrimethylsilane in an inert organic solvent such as acetonitrile;

(xix) compounds containing 1,1-difluoroalkyl or trifluoromethyl group(s) can be prepared from compounds containing alkanoyl or carboxy group(s) by reaction with a fluorinating agent such as sulphur tetrafluoride or a modified reagent such as diethylaminosulphur trifluoride and potassium fluoride at a temperature from 0° C. to 100° C. in an inert organic solvent such as 2-methoxyethyl ether;

(xx) compounds containing cyano group(s) can be prepared by dibromination of methyl group(s) using for example N-bromosuccimide optionally in the presence of a radical initiator such as dibenzoyl peroxide, followed by hydrolysis of the corresponding dibromomethyl derivative to a formyl group, followed by reaction with hydroxylamine, optionally as the hydrochloride, in aqueous-alcoholic medium, followed by dehydration of the corresponding oxime using for example phosphorus oxychloride;

(xxi) agriculturally acceptable salts as hereinbefore described can be prepared by the reaction of an acidic or basic compound of general formula I with a suitable base or with a suitable acid respectively.

It will be appreciated that in the preparation of compounds of general formula I the foregoing processes or adaptations thereof may be performed in an appropriate combination to achieve the compound sought, e.g. (vii)+(iv)+(viii)+(ix)(affording compounds of general formula I wherein $R^2$=cyano, $R^3$=halogen).

Compounds of general formula I as hereinbefore defined not hitherto disclosed or described in the chemical literature with the exclusion of compounds in which $R^2$ and $R^3$ simultaneously represent hydrogen atoms, together with their processes of preparation and compositions which contain them, form further features of the present invention. Medicated feeds which comprise known compounds of general formula I or pesticidally-acceptable salts thereof, and an edible carrier or diluent form a further feature of the present invention.

Compounds of general formula I in which $R^2$ and $R^3$ simultaneously represent hydrogen atoms are intermediates for the preparation of compounds for use in the method of the invention; they and their processes of preparation form further features of the present invention. Intermediates of general formula I in which $R^2$ and $R^3$ simultaneously represent hydrogen atoms may be prepared by the reaction of the corresponding benzaldehyde with glyoxal in the presence of ammonia or ammonium acetate, followed if appropriate by N-alkylation as hereinbefore described.

Compounds of general formula IV may be prepared by the application or adaptation of known methods, for example the reaction of the corresponding benzaldehyde with a compound of general formula $R^9(NH_2)C=C(CN)NH_2$. The compounds of general formula IV and their preparation form further features of the present invention.

Compounds of general formula $R^9(NH_2)C=C(CN)NH_2$ are known or may be prepared by the application or adaptation of known methods.

The following Examples illustrate the preparation of compounds of general formula I shown in Figure I and the Reference Examples illustrate the preparation of intermediates.

EXAMPLE 1

Compound A

A solution of 1-amino-2-(2,6-dichloro-4-trifluoromethylbenzylbenzylideneamino)-1,2-dicyanoethylene (3.3 g, 0.01 mol) and 2,3-dichloro-5,6-dicyano-1,4-benzoquinone (3.3 g, 0.01 mol) in acetonitrile (75 ml) was stirred at reflux for 48 hours. Evaporation of the solvent yielded a brown solid which was continuously extracted with boiling toluene. The solution was evaporated under reduced pressure and the red-brown residue was dissolved in a mixture of ethyl acetate and dichloromethane (1:10) and filtered through silica. Evaporation of the filtrate gave a brown solid which was triturated with hexane and the solid was removed by filtration to give 2-(2,6-dichloro-4-trifluoromethylphenyl)-4,5- dicyanoimidazole (1.4 g) as a light brown solid, m.p. 194°–195° C.

REFERENCE EXAMPLE 1

Diaminomaleonitrile (4.4 g, 0.04 mol) was dissolved in methanol (100 ml) and 2,6-dichloro-4-trifluoromethylbenzaldehyde (9.6 g, 0.04 mol) was added with stirring at ambient temperature. The reaction mixture was stirred for 30 minutes and heated at reflux for 1 hour. After cooling to 10° C. a solid which had separated was filtered off to give 1-amino-2-(2,6-dichloro-4-trifluoromethylbenzylideneamino)- 1,2-dicyanoethylene (10.3 g) as a yellow crystalline solid, m.p. 218°–219° C.

REFERENCE EXAMPLE 2

1-Bromo-2,6-dichloro-4-trifluoromethylbenzene (80 g, 0.27 mol) was dissolved in anhydrous diethyl ether (480 ml) and the solution was cooled to −78° C. Butyllithium (2.5M solution in hexane, 100 ml) was added dropwise with stirring in an atmosphere of nitrogen while maintaining the temperature below −70° C. After stirring for a further 1 hour at −78° C. N-formylpiperidine (30.8 g, 0.27 mol) was added dropwise. The mixture was stirred at −78° C. overnight and allowed to warm slowly to 0° C. Hydrochloric acid (2M, 200 ml) was added dropwise to the solution with ice-cooling. The two layers were separated and the organic phase was washed with water, dried over anhydrous sodium sulphate and evaporated to dryness. The oily residue was dissolved in a mixture of ethyl acetate and petroleum spirit (b.p. 60°–80° C.) (1:10) and the solution was filtered through a column of silica. Evaporation of the filtrate and distillation of the resultant oil gave 2,6-dichloro-4-trifluoromethylbenzaldehyde (43.7 g) as a colourless liquid, b.p. 115° C. at 14 mmHg.

REFERENCE EXAMPLE 3

Nitrosyl sulphuric acid, prepared from sodium nitrite (69 g, 1 mol) and concentrated sulphuric acid (600 ml) was added dropwise with stirring to a cooled solution of 2,6-dichloro-4-trifluoromethylaniline (230 g, 1 mol) in glacial acetic acid (1250 ml) at 15°–20° C. The mixture was stirred for 1 hour at ambient temperature. The diazonium mixture was run slowly into a solution prepared from cuprous bromide (143.4 g, 1 mol), hydrobromic acid (48%, 1 l) and ice (approx. 1000 g) at a rate so as not to exceed a temperature of 35° C. After 1 hour the mixture was steam distilled to give 1 l of distillate which was diluted with water (3 l) and extracted with diethyl ether (2×500 ml). The organic fractions were combined and washed with aqueous sodium hydroxide solution (2M, 2×250 ml) and water (250 ml), dried over anhydrous sodium sulphate and evaporated to dryness. The oily residue was distilled to give 1-bromo-2,6-dichloro-4-trifluoromethylbenzene (256.8 g) as a colourless liquid, b.p. 74°–78° C. at 6 mmHg.

EXAMPLE 2

Compounds B and C

By proceeding in a similar manner to that hereinbefore described in Example 1 but replacing 1-amino-2-(2,6-dichloro-4-trifluoromethylbenzylideneamino)-1,2-dicyanoethylene with the following starting materials there were prepared: 2-(2,6-dichloro-4-trifluoromethoxyphenyl)-4,5-dicyanoimidazole which was recrystallised from toluene as an off-white solid, m.p. 119.5°–122.5° C., from 1-amino-2-(2,6-dichloro-4-trifluoromethoxybenzylideneamino)-1,2-dicyanoethylene; and 2-(2-chloro-4-trifluoromethylphenyl)-4,5-dicyanoimidazole which was recrystallised from toluene as a cream solid, m.p. 163°–164° C., from 1-amino-2-(2-chloro-4-trifluoromethylbenzylideneamino)-1,2-dicyanoethylene.

REFERENCE EXAMPLE 4

By proceeding in a similar manner to that hereinbefore described in Reference Example 1 but replacing 2,6-dichloro-4-trifluoromethylbenzaldehyde with the following starting materials there were prepared: 1-amino-2-(2,6-dichloro-4-trifluoromethoxybenzylideneamino)-1,2-dicyanoethylene as a yellow crystalline solid, m.p. 108°–112° C., from 2,6-dichloro-4-trifluoromethoxybenzaldehyde; and 1-amino-2-(2-chloro-4-trifluoromethoxybenzylideneamino)-1,2-dicyanoethylene as a yellow crystalline solid, m.p. 197°–199° C., from 2-chloro-4-trifluoromethylbenzaldehyde.

REFERENCE EXAMPLE 5

By proceeding in a similar manner to that hereinbefore described in Reference Example 2 but replacing 1-bromo-2,6-dichloro-4-trifluoromethylbenzene with the following starting materials there were prepared: 2,6-dichloro-4-trifluoromethoxybenzaldehyde as a pale yellow liquid b.p. 113° C. at 20 mm Hg from 1-bromo-2,6-dichloro-4-trifluoromethoxybenzene; and 2-chloro-4-trifluoromethylbenzaldehyde as a colourless liquid b.p. 67°–71° C. at 8 mm Hg from 1-bromo-2-chloro-4-trifluoromethylbenzene.

REFERENCE EXAMPLE 6

By proceeding in a similar manner to that hereinbefore described in Reference Example 3 but replacing 2,6-dichloro-4-trifluoromethylaniline with the following starting materials there were prepared: 1-bromo-2,6-dichloro-4-trifluoromethoxybenzene as a colourless liquid b.p. 54°–58° C. at 3 mm Hg from 2,6-dichloro-4-trifluoromethoxyaniline; and 1-bromo-2-chloro-4-trifluoromethylbenzene as a colourless liquid b.p. 55°–58° C. at 8 mm Hg from 2-chloro-4-trifluoromethylaniline.

EXAMPLE 3

Compound D 1,1-Dibromo-3,3,3-trifluoroacetone (59.4 g, 0.22 mol) was added to a solution of sodium acetate trihydrate (59.8 g, 0.44 mol) in water (200 ml) and the resultant solution was heated on a steam bath for 30 minutes. After cooling to room temperature, the cloudy solution was added with stirring to a solution of 2,6-dichloro-4-trifluoromethylbenzaldehyde (48.6 g, 0.2 mol) in methanol (500 ml) and aqueous ammonia (33%, 250 ml) and the red suspension was stirred at room temperature overnight. The supernatant liquid was decanted from the insoluble gum and evaporated to a quarter of the volume. Water (200 ml) was added and the solid was filtered off and recrystallised from a mixture of methanol and water to give 2-(2,6-dichloro-4-trifluoromethylphenyl)-4-trifluoromethylimidazole (14.0 g) as a light brown solid, m.p. 213°–215° C.

EXAMPLE 4

Compound E

A solution of 2-(2,6-dichloro-4-trifluoromethylphenyl)-4-trifluoromethylimidazole (0.7 g, 0.002 mol)

and bromine (0.32 g, 0.1 ml, 0.002 mol) in glacial acetic acid (5 ml) was stirred and heated at reflux for 2 hours. The cooled suspension was poured into cold water (50 ml) and the solid was filtered and washed with water. The solid was dissolved in glacial acetic acid (5 ml) and bromine (0.32 g, 0.1 ml, 0.002 mol) was added. The mixture was stirred and heated at reflux for 2 hours, cooled and poured into cold water (50 ml). The solid was filtered and washed thoroughly with water to give 5-bromo-2-(2,6-dichloro-4-trifluoromethylphenyl)-4-trifluoromethylimidazole (0.6 g) as a white solid, m.p. 295° C. with decomposition.

EXAMPLE 5

Compound F

A mixture of 2-(2,6-dichloro-4-trifluoromethylphenyl)-4-trifluoromethylimidazole (1.0 g, 0.0027 mol) in fuming nitric acid (95%, 1 ml) and fuming sulphuric acid (30% free $SO_3$, 1 ml) was stirred and heated at 120° C. for 3.5 hours. The mixture was poured into cold water (50 ml) and the solid was filtered off and washed with water. The resultant solid was purified by chromatography on silica gel, eluting with a mixture of ethyl acetate and n-hexane (1:5) to give 2-(2,6-dichloro-4-trifluoromethylphenyl)-5-nitro 4-trifluoromethylimidazole (0.7 g) as an off-white solid, m.p. 244°-252° C.

EXAMPLE 6

Compound G

A solution of 2-(2,6-dichloro-4-trifluoromethylphenyl)-4,5-dicyanoimidazole (25.3 g, 0.08 mol) in absolute ethanol (80 ml) and concentrated hydrochloric acid (30 ml) was heated at reflux for 69 hours. The mixture was poured into cold water (200 ml) and extracted with dichloromethane (2×150 ml). The combined organic layers were extracted with saturated aqueous sodium bicarbonate (2×200 ml) which was acidified carefully to pH 3 and extracted with dichloromethane (100 ml). The aqueous layer was acidified to pH 1 and extracted with ethyl acetate (2×100 ml), washed with water (100 ml), dried over anhydrous sodium sulphate and evaporated to dryness. The gummy residue was treated with dichloromethane (50 ml) and evaporated to dryness to give 5-cyano-2-(2,6-dichloro-4-trifluoromethylphenyl)imidazole-4-carboxylic acid (6.31 g) as an off-white solid which decomposed at 80°-130° C.

EXAMPLE 7

Compound H

A solution of 5-cyano-2-(2,6-dichloro-4-trifluoromethylphenyl)imidazole-4-carboxylic acid (7.09 g, 0.02 mol) in diethyleneglycol (70 ml) was stirred and heated at 170° C. in an atmosphere of nitrogen for 36 hours. The reaction mixture was cooled to room temperature and water (150 ml) was added. The reaction mixture was extracted with ethyl acetate (2×100 ml), washed with water (50 ml), dried over anhydrous sodium sulphate and evaporated to dryness. The solid residue was purified by chromatography on silica gel eluting with a mixture of ethyl acetate and petroleum ether (b.p. 60°-80° C.)(1:1) and recrystallised from a mixture of ethyl acetate and petroleum ether (b.p. 60°-80° C.) to give 5-cyano-2-(2,6-dichloro-4-trifluoromethylphenyl)imidazole (2.15 g) as a white solid m.p. 210°-212° C.

EXAMPLE 8

Compound I

A mixture of 5-cyano-2-(2,6-dichloro-4-trifluoromethylphenyl)imidazole (1.0 g, 0.0033 mol) and bromine (1.9 g, 0.64 ml, 0.13 mol) in 1,1,2,2-tetrachloroethane (20 ml) was stirred and heated at 90° C. for 7 hours. Ethyl acetate (50 ml) was added and the solution was washed with water (50 ml), aqueous sodium metabisulphite solution (50 ml), water (50 ml), dried over anhydrous sodium sulphate and evaporated to dryness. The solid residue was purified by chromatography on silica gel eluting with a mixture of ethyl acetate and petroleum ether (b.p. 60°-80° C.)(3:10) to give 4-bromo-5-cyano-2-(2,6-dichloro-4-trifluoromethylphenyl)imidazole (2.15 g) as a white solid m.p. 270.5°-272° C.

EXAMPLE 9

Compounds J and K

A mixture of 2-(2,6-dichloro-4-trifluoromethylphenyl)-4,5-dicyanoimidazole (3.31 g, 0.01 mol) and sodium hydroxide (1.0 g, 0.025 mol) in water (10 ml) was stirred and heated at 40° C. overnight. Concentrated hydrochloric acid was added to the mixture and the precipitated solid was filtered off and purified by medium pressure liquid chromatography (mplc) on silica eluted with a mixture of ethyl acetate and dichloromethane (1:1). Recrystallization of the white solid from a mixture of ethyl acetate and petroleum spirit (bp 60°-80° C.) (1:1) gave 5-cyano-2-(2,6-dichloro-4-trifluoromethylphenyl)-imidazole-4-carboxamide (0.61 g), m.p. 254°-255° C., as a white solid.

By proceeding in a similar manner but replacing 2-(2,6-dichloro-4-trifluoromethylphenyl)-4,5-dicyanoimidazole with 2-(2,6-dichloro-4-trifluoromethoxyphenyl)-4,5-dicyano-imidazole: 5-cyano-2-(2,6-dichloro-4-trifluoromethoxyphenyl)imidazole-4-carboxamide, m.p. 220°-222.5° C. as a white solid.

EXAMPLE 10

Compound L

A mixture of 2-(2,6-dichloro-4-trifluoromethylphenyl)-4,5-dicyanoimidazole (3.3 g, 0.01 mol), ethanol (10 ) and concentrated hydrochloric acid (10 ml) was stirred and heated at reflux for 24 hours. After cooling the mixture was poured into water (50 ml) and extracted with dichloromethane (2×50 ml). The combined extracts were washed with water (50 ml), dried over anhydrous sodium sulphate and evaporated to dryness. The residue was purified by mplc on silica eluted with a mixture of ethyl acetate and petroleum spirit (b.p. 60°-80° C.) (1:1) to give ethyl 5-cyano-2-(2,6-dichloro-4-trifluoromethylphenyl)-imidazole-4-carboxylate (0.35 g) m.p. 180°-181° C., after recrystallisation from a mixture of toluene and petroleum spirit (b.p. 60°-80° C.) (1:2), as a white solid.

EXAMPLE 11

Compound M

A mixture of 2-(2,6-dichloro-4-trifluoromethylphenyl)-4,5-dicyanoimidazole (3.3 g, 0.01 mol) and potassium hydroxide (85%, 1.64 g, 0.025 mol) in ethanol (20 ml) and water (2 ml) was heated at reflux for 3.5 hours. After cooling the mixture was poured into water (100 ml) and acidified to pH1 by the addition of concentrated hydrochloric acid. The precipitated solid was filtered off and dried at 80° C. and 10 mm Hg to give 2-(2,6-dichloro-4-trifluoromethylphenyl)-imidazole-4,5-dicarboxamide (0.6 g), m.p. 306°-308° C., as an off white solid.

EXAMPLE 12

Compound N

A mixture of 2,6-dichloro-4-trifluoromethylbenzaldehyde (5.0 g, 0.02 mol), butan-2,3-dione (1.7 g, 0.02 mol), ammonium acetate (16.0 g, 0.2 mol), and acetic acid (40 ml) was heated at reflux for 6 hours. The mixture was evaporated to low volume and was poured into water (100 ml). The mixture was neutralized to pH7 and the precipitated solid was filtered off to give 2-(2,6-dichloro-4-trifluoromethylphenyl)-4,5-dimethylimidazole (0.5 g), m.p. 281°-282° C., after re-crystallisation from a mixture of toluene and petroleum spirit (b.p. 60°-80° C.) (1:1), as a white solid.

EXAMPLE 13

Compound O

Pyruvicaldehyde (40% aqueous solution, 50 ml) was added dropwise to a solution of 2,6-dichloro-4-trifluoromethylbenzaldehyde (12.15 g, 0.05 mol) in methanol (150 ml) and aqueous ammonia (30%, 100 ml) whilst stirring and heating at reflux. The mixture was stirred and heated at reflux for a further 2 hours, cooled and the supernatant solution decanted from the gummy glass. The solution was evaporated and extracted with dichloromethane (3×100 ml). The combined extracts were washed with water (2×75 ml), dried over anhydrous sodium sulphate and evaporated to dryness. The residue was purified by mplc on silica eluted with a mixture of ethyl acetate and dichloromethane (1:4) to give 2-(2,6-dichloro-4-trifluoromethylphenyl)-4-methylimidazole (1.7 g) m.p. 211°-212° C., after re-crystallisation from a mixture of toluene and petroleum spirit (bp 60°-80° C.) (1:2), as an off-white solid.

EXAMPLE 14

Compound P

A mixture of 2-(2,6-dichloro-4-trifluoromethylphenyl)-4-methylimidazole (1.0 g, 0.003 mol), nitric acid (70% w/w, 1 ml) and sulphuric acid (98% w/w, 1 ml) was stirred and heated at 75° C. for 4 hours then at 100° C. for 2 hours. After cooling the reaction mixture was added to a mixture of ice and water (20 ml) and the precipitated solid was filtered off. Recrystallisation from toluene gave 2-(2,6-dichloro-4-trifluoromethylphenyl)-4-methyl-5-nitroimidazole (0.66 g), m.p. 316.5°-317.5° C., as a white solid.

EXAMPLE 15

Compound O

Aqueous ammonia solution (approximately 33% w/w, 1.2 ml) was added dropwise with stirring to a solution of 2-(2,6-dichloro-4-trifluoromethylphenyl)-4-methylimidazole-5-sulphonyl chloride (2.0 g, 0.005 mol) in dioxane (15 ml) and the mixture was stirred for 3 hours. It was poured into water (50 ml) and extracted with diethyl ether (3×25 ml). The combined extracts were washed with water (2×50 ml) dried over anhydrous sodium sulphate and evaporated to dryness. The residue was purified by mplc on silica eluted with a mixture of ethyl acetate and petroleum spirit (bp 60°-80° C.) (1:2). Recrystallization from a mixture of ethyl acetate and petroleum spirit (b.p. 60°-80° C.) (1:3) gave 2-(2,6-dichloro-4-trifluoromethylphenyl)-4-methylimidazole-5-sulphonamide (0.45 g), m.p. 266°-267° C., as an off-white solid.

EXAMPLE 16

Compound R

A solution of stannous chloride dihydrate (18.62 g, 0.08 mol), in hydrochloric acid (36% w/w), 16 ml) was added dropwise with stirring to a suspension of 2-(2,6-dichloro-4-trifluoromethylphenyl)-4-methylimidazole-5-sulphonyl chloride (6.65 g, 0.017 mol) in acetic acid (100 ml) in an atmosphere of nitrogen whilst heating at 70° C. Stirring and heating at 70° C. was continued for 22 hours. After cooling the mixture was poured into a mixture of water (350 ml) and hydrochloric acid (36% w/w, 5.3 ml) and extracted with ethyl acetate (3×100 ml). The combined extracts were washed with water (2×100 ml) dried over anhydrous sodium sulphate and evaporated to dryness. The residue was dissolved in aqueous sodium hydroxide solution (20% w/w, 20 ml) and filtered to remove insoluble material. The solution was diluted with water (70 ml) and heated with iodomethane (9.3 g, 0.065 ml) with stirring in an atmosphere of nitrogen. After 22 hours the mixtures was extracted with ethyl acetate (4×50 ml). The combined extracts were washed with water (2×50 ml) dried over anhydrous sodium sulphate and evaporated to dryness. The residue was purified by mplc on silica eluted with a mixture of ethyl acetate and petroleum spirit (b.p. 60°-80° C. (1:5) to give after re-crystallization from toluene 2-(2,6-Dichloro-4-trifluoromethylphenyl)-4-methyl-5-methylthioimidazole (0.18 g) m.p. 243°-244°, as a white solid.

REFERENCE EXAMPLE 7

2-(2,6-Dichloro-4-trifluoromethylphenyl)-4-methylimidazole (1.0 g, 0.0034 mol) was added portionwise to chlorosulphonic acid (3 ml) and the mixture was stirred and heated at 100° C. for 2 hours. After cooling thionyl chloride (0.2 ml) was added and the mixture was reheated to 100° C. for 2 hours. The mixture was added cautiously to ice (20 g), and extracted with ethyl acetate (2×20 ml). The combined extracts were washed with water (20 ml) dried over anhydrous sodium sulphate and evaporated to dryness. Recystallisation from a mixture of ethyl acetate and petroleum spirit (bp 60°-80° C.)(1:3) gave 2-(2,6-dichloro-4-trifluoromethylphenyl)-4-methylimidazole-5-sulphonyl chloride (0.21 g), m.p. 227°-230° C. as an off-white solid.

EXAMPLE 17

Compound S

A mixture of 2-(2,6-dichloro-4-trifluoromethylphenyl)imidazole (5.62 g, 0.02 mol), nitric acid (70% w/w, 5.6 ml) and sulphuric acid (98% w/w, 5.6 ml) was stirred and heated at 70° C. for a total of 51 hours. After cooling the reaction mixture was poured into a mixture of ice and water (approximately 75 ml) and the precipitated solid was filtered off. It was purified by mplc on silica eluted with a mixture of ethyl acetate and dichloromethane (1:20) to give 2-(2,6-dichloro-4-trifluoromethylphenyl)-4-nitroimidazole (4.21 g), m.p. 254°-255° C., as a cream crystalline solid.

EXAMPLE 18

Compound T

N-Bromosuccinimide (5.07 g, 0.028 mol) was added portionwise to a solution of 2-(2,6-dichloro-4-trifluoromethylphenyl)imidazole (4.0 g, 0.014 mol) in chloroform (300 ml) with stirring. Stirring was continued for 6 hours and the precipitated solid filtered off to give 4,5-dibromo-2-(2,6-dichloro-4-trifluoromethylphenyl)-imidazole (4.46 g) m.p. 328°–329° C., as an off-white solid.

EXAMPLE 19

Compound U

A solution of N-bromosuccinimide (0.63 g, 0.0036 mol) in dimethylformamide (dried over 4Å molecular sieve, 18 ml was added dropwise with stirring to a solution of 2-(2,6-dichloro-4-trifluoromethylphenyl)-imidazole (1.0 g, 0.0036 mol) in dimethylformamide (dried over 4Å molecular sieve, 18 ml) and stirred for 7 hours. The mixture was poured into water (180 ml) and extracted with dichloromethane (5×30 ml). The combined extracts were washed with water (3×50 ml), dried over anhydrous sodium sulphate and evaporated to dryness. The residue was purified by mplc on silica eluted with a mixture of ethyl acetate and petroleum spirit (bp 60°–80° C.) (3:5) to give 4-bromo-2-(2,6-dichloro-4-trifluoromethylphenyl)-imidazole (0.17 g), m.p. 224°–225° C., as an off-white solid.

REFERENCE EXAMPLE 8

Glyoxal (40% w/w aqueous solution, 160 ml, 1.1 mol) was added dropwise with stirring to a mixture of 2,6-dichloro-4-trifluoromethylbenzaldehyde (48.6 g, 0.2 mol), methanol (600 ml) and ammonia (33% w/w aqueous solution, 400 ml) over 4 h whilst heating the mixture at reflux. The mixture was stirred and heated at reflux for 2 hours, cooled and the methanol was removed by evaporation. The aqueous residue was extracted with dichloromethane (5×250 ml) and the combined extracts were washed with water (3×250 ml), dried over anhydrous sodium sulphate and evaporated to dryness. The residue was purified by mplc on silica eluted with a mixture of ethyl acetate and dichloromethane (1:10) to give, after recrystallisation from ethyl acetate 2-(2,6-dichloro-4-trifluoromethylphenyl)-imidazole (6.24 g) mp 193°–194° C. as a light brown solid.

EXAMPLE 20

Compound V

A mixture of 4-bromo-2-(2,6-dichloro-4-trifluoromethylphenyl)-imidazole (0.9 g, 0.025 mol), nitric acid (70% w/w, 1 ml) and sulphuric acid (98% w/w, 1 ml) was stirred and heated at 70° C. for 7.5 hours. After cooling it was added to a mixture of ice and water (50 ml). The precipitated solid was filtered off and purified by mplc on silica eluted with a mixture of ethyl acetate and petroleum spirit (b.p. 60°–80° C.) (1:5) to give 4-bromo-2-(2,6-dichloro-4-trifluoromethylphenyl)-5-nitro-imidazole (0.2 g), m.p. 292°–293° C., as an off-white solid.

EXAMPLE 21

Compounds W and Y

By proceeding in a similar manner to that hereinbefore described in Example 1 but replacing 1-amino-2-(2,6-dichloro-4-trifluoromethylbenzylideneamino)-1,2-dicyanoethylene with the following starting materials there were prepared: 2-(2-bromo-4-trifluoromethylphenyl)-4,5-dicyanoimidazole as a white solid after trituration with hexane-ethyl acetate, m.p. 139°–140° C., from 1-amino-2-(2-bromo-4-trifluoromethylbenzylideneamino)-1,2-dicyanoethylene; and 2-(2,3,5,6-tetrachloro-4-trifluoromethylthiophenyl)-4,5-dicyanoimidazole which was recrystallised from toluene as a white solid, m.p. 245°–246.5° C., from 1-amino-2-(2,3,5,6-tetrachloro-4-trifluoromethylthiobenzylideneamino)-1,2-dicyanoethylene.

REFERENCE EXAMPLE 9

By proceeding in a similar manner to that hereinbefore described in Reference Example 1 but replacing 2,6-dichloro-4-trifluoromethylbenzaldehyde with the following starting materials there were prepared: 1-amino-2-(2-bromo-4-trifluoromethylbenzylideneamino)-1,2-dicyanoethylene as a sticky yellow solid from 2-bromo-4-trifluoromethylbenzaldehyde; 1-amino-1,2-dicyano-2-(2,3,5,6-tetrachloro-4-trifluoromethylthiobenzylideneamino)ethylene as a yellow crystalline solid re-crystallized from toluene m.p. 191°–191.5° C. from 2,3,5,6-tetrachloro-4-trifluoromethylthiobenzaldehyde.

REFERENCE EXAMPLE 10

2,3,5,6-Tetrachloro-4-trifluoromethylthiobenzyl bromide (6.48 g, 0.016 mol) was added to a mixture of 2-nitropropane (1.95 g, 0.021 mol) and sodium ethoxide in ethanol (from sodium, 0.36 g, 0.016 mol and ethanol, 95 ml). The mixture was stirred at room temperature for 66 hours and evaporated to dryness. The residue was treated with water (50 ml) and extracted with diethyl ether (2×50 ml). The combined extracts were washed with aqueous sodium hydroxide solution (5%, 50 ml), water (2×75 ml), dried over anhydrous magnesium sulphate and evaporated to dryness. The residue was purified by mplc on silica eluting with n-hexane to give 2,3,5,6-tetrachloro-4-trifluoromethylthiobenzaldehyde (2.79 g) m.p. 98.5°–100° C. as a white solid.

REFERENCE EXAMPLE 11

By proceeding in a similar manner to that hereinbefore described in Reference Example 10 but replacing 2,3,5,6-tetrachloro-4-trifluoromethylthiobenzyl bromide with the following starting material there was prepared: 2-bromo-4-trifluoromethylbenzaldehyde as a mobile yellow oil [NMR (CDCl$_3$) chemical shift 7.5–8.2 ppm (multiplet, 3H); 10.3 ppm (s, 1H)] from 2-bromo-4-trifluoromethylbenzyl bromide.

REFERENCE EXAMPLE 12

A mixture of 2,3,5,6-tetrachloro-4-trifluoromethylthiotoluene (13.46 g, 0.041 mol) and N-bromosuccinimide (7.26 g, 0.041 mol) in carbon tetrachloride (34 ml) was stirred and heated at reflux for 21 hours. After cooling the mixture was filtered and the filtrate washed with aqueous sodium hydroxide solution (5%, 2×100 ml), water (100 ml), dried over anhydrous magnesium sulphate and evaporated to dryness. Recrystallization of the residue gave 2,3,5,6-tetrachloro-4-trifluoromethylthiobenzyl bromide (8.17 g) m.p. 117°–118.5° C. as a white crystalline solid. By proceeding in a similar manner but replacing 2,3,5,6-tetrachloro-4-trifluoromethylthiotoluene with the following starting material there was prepared: 2-bromo-4-trifluoromethylbenzyl bromide as a mobile yellow oil from 2-bromo-4-trifluoromethyltoluene.

2-methyl-5-trifluoromethylaniline (10.1 g) was dissolved in hydrobromic acid (50%; 50 ml) and treated with sodium nitrite (2.8 g) at 0°-5° C. The diazonium solution was treated with cuprous bromide (8.6 g) dissolved in hydrobromic acid (50 ml) and the solution was allowed to warm to ambient temperature and was steam distilled.

The distillate was extracted with ether (3×100 ml) and the contained combined extracts were dried over sodium sulphate filtered and evaporated to give an oil which was distilled to give 2-bromo-4-trifluoromethyltoluene (9.5 g) b.p. 98°-101° C./45 mm Hg.

2-Methyl-5-trifluoromethylnitrobenzene (14.8 g) was dissolved in ethanol (100 ml) and hydrogenated at ambient temperature and pressure in the presence of palladium on charcoal (10%; 0.5 g). The solution was filtered and evaporated to dryness to give 2-methyl-5-trifluoromethylaniline (10.1 g) as a pale yellow oil.

4-Trifluoromethyltoluene (12.8 g) was treated at 60°-70° C. with a mixture of concentrated nitric acid (25 ml) and concentrated sulphuric acid (25 ml) for 5 hours. The solution was poured onto ice (0.5 litres) and extracted with ether (3×100 ml). The combined ether extracts were washed with water, dried over sodium sulphate, filtered and evaporated to dryness to give 2-methyl-5-trifluoromethylnitrobenzene (14.8 g) as a pale yellow oil.

4-Trifluoromethylbenzaldehyde (20.0 g) was dissolved in acetic acid (100 ml) and treated with hydrogen in the presence of platinum (0.5 g) at ambient temperature and pressure for 10 hours. The solution was filtered, poured into water (400 ml), basified by addition of aqueous sodium hydroxide solution (2 M), extracted with ether (3×100 ml). The combined extracts were washed with water (2×100 ml), dried over anhydrous magnesium sulphate, evaporated to dryness. The residue was distilled to give 4-trifluoromethyltoluene (14.3 g) b.p. 131°-132° C. as a colourless mobil liquid.

REFERENCE EXAMPLE 13

Chlorine gas was bubbled through a mixture of 4-trifluoromethylthiotoluene (10 g, 0.052 mol) and anhydrous ferric chloride (2.3 g, 0.014 mol) in dry dichloromethane (300 ml) for 1.7 hours during which time the temperature rose to 30° C. Nitrogen was bubbled through the mixture to remove excess chlorine and the mixture was washed with water (4×200 ml), dried over anhydrous magnesium sulphate and evaporated to dryness. The residue was recrystallized from aqueous ethanol (1:1) to give 2,3,5,6-tetrachloro-4-trifluoromethylthiotoluene (16.25 g) m.p. 49.5°-50.5° C. as colourless prisms.

EXAMPLE 22

Compound Z

A solution of iodotrimethylsilane (2.83 g, 0.014 mol) in acetonitrile (5 ml) was added dropwise with stirring to a suspension of 4-(tert.butoxycarbonylamino)-5-cyano-2-(2,4-dichlorophenyl)imidazole (5.0 g, 0.014 mol) in acetonitrile (250 ml) whilst maintaining the temperature at about 0° C. The mixture was stirred at room temperature for 48 hours and the precipitated beige solid filtered off. The solid was purified by mplc on silica eluting with a mixture of ethyl acetate and hexane (1:2) to give an off-white solid which was recrystallized from ethanol to give 4-amino-5-cyano-2-(2,4-dichlorophenyl)imidazole (1.35 g) m.p. 223°-225° C. as an off-white solid.

EXAMPLE 23

Compound BB

A mixture of 5-cyano-2-(2,4-dichlorophenyl)imidazole-4-carboxylic acid (40.0 g, 0.142 mol), diphenylphosphoryl azide (37.0 g, 0.142 mol) and triethylamine (14.4 g, 19.8 ml, 0.142 mol) in 2-methyl-2-propanol (dried by distillation from calcium hydride, 1400 ml) was heated at reflux for 24 hours. After cooling the mixture was filtered and the filtrate evaporated to dryness. The residue was dissolved in ethyl acetate (2250 ml) and washed with hydrochloric acid (1 M, 250 ml) saturated aqueous sodium bicarbonate solution (2×250 ml) dried over anhydrous magnesium sulphate and evaporated to dryness. The residue was recrystallized from ethanol to give 4-tert.butoxycarbonylamino)-5-cyano-2-(2,4-dichlorophenyl)imidazole (22.2 g) m.p. 185° C. (with decomposition) as an off-white solid.

EXAMPLE 24

Compound CC

By proceeding in a similar manner to that hereinbefore described in Example 6 but replacing 2-(2,6-dichloro-4-trifluoromethylphenyl)-4,5-dicyanoimidazole with the following starting material there was prepared: 5-cyano-2-(2,4-dichlorophenyl)imidazole-4-carboxylic acid m.p. 206°-209° C. (with decomposition) from 2-(2,4-dichlorophenyl)-4,5-dicyanoimidazole.

EXAMPLE 25

Compound AA

N,N-Diethylaminosulphur trifluoride (11.4 ml, 0.086 mol) was added dropwise to a stirred solution of 2-(2,4-dichlorophenyl)imidazole-4,5-dicarboxylic acid (5.05 g, 0.017 mol) in 2-methoxyethyl ether (18 ml) whilst maintaining the temperature below 0° C. Sodium fluoride (1.82 g, 0.040 mol) was added and the mixture stirred and heated at 80°-85° C. for 41 hours. The mixture was added to water (100 ml) and extracted with dichloromethane (2×100 ml). The combined extracts were washed with water (100 ml), dried over anhydrous magnesium sulphate and evaporated to dryness. The residue was purified by mplc on silica eluting with a mixture of ethyl acetate and n-hexane (1:2) to give N,N-diethyl 2-(2,4-dichlorophenyl)-5-trifluoromethylimidazole-4-carboxamide (0.27 g) m.p. 186.5°-190° C. as an off-white solid.

EXAMPLE 26

Compound DD

A mixture of 2-(2,4-dichlorophenyl)-4,5-dicyanoimidazole (10.05 g, 0.038 mol), glacial acetic acid (41 ml), concentrated sulphuric acid (19 ml) and water (9.4 ml) was heated at 120°-125° C. for 1.5 hours. After cooling the mixture was poured into water (300 ml) and the precipitated solid filtered off and dried in vacuo (100° C. at 50 mm Hg) to give 2-(2,4-dichlorophenyl)imidazole-4,5-dicarboxylic acid (10.24 g) m.p. 237.5°-238.5° C. as a white solid.

EXAMPLE 27

Compound X

Diethylaminosulphur trifluoride (1.5 ml) was added dropwise to a stirred suspension of 5-cyano-2-(2,6-dichloro-4-trifluoromethylphenyl)imidazole-4-carboxylic acid (1.4 g, 0.004 mol) in 2-methoxyethyl ether (11 ml) whilst maintaining the temperature at about 0° C. Potassium fluoride (0.67 g, 0.0115 mol) was added and the mixture was stirred at 0° C. for 0.5 hours, and added slowly to a solution of diethylamine (8.8 g, 12.5 ml, 0.12 mol) in dichloromethane (75 ml) whilst maintaining the temperature in the range 0°-5° C. The mixture was stirred at 0°-5° C. for 1 hour and at room temperature for 0.5 hours. The mixture was washed with saturated aqueous sodium bicarbonate solution (50 ml), dried over anhydrous sodium sulphate and evaporated to dryness. The residue was purified by mplc on silica eluting with a mixture of ethyl acetate and dichloromethane (1:2) to give N,N-diethyl 5-cyano-2-(2,6-dichloro-4-trifluoromethylphenyl)imidazole-4-carboxamide (0.26 g) m.p. 195°-197° C. as an off-white solid.

In experiments on activity against arthropods carried out on representative compounds of general formula I, the following results (wherein ppm indicates the concentration of the compound in parts per million of the test solution applied) have been obtained:-

One or more dilutions of the compounds to be tested were made in 50% aqueous acetone. Test species: *Plutella xylostella* (Diamond-back Moth)

Turnip leaf discs were set in agar in petri-dishes and infected with 10 2nd instar Plutella larvae. Four replicate dishes were assigned to each treatment and were sprayed under a Potter Tower with the appropriate test dilution. Four or five days after treatment the dishes were removed from the constant temperature (25° C.) room in which they had been held and the mean percentage mortalities of larvae were determined. These data were corrected against the mortalities in dishes treated with 50% aqueous acetone alone which served as controls.

The compounds listed below all gave more than 90% mortality of *Plutella xylostella* larvae when these were treated with a dilution of 100 ppm. Compound A, B, C, E, F and T.

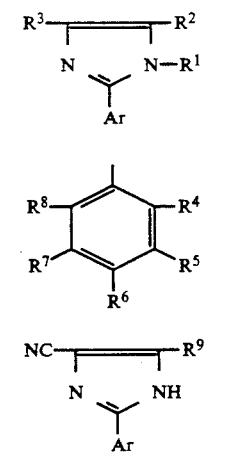

R⁹(NH₂)C=C(CN)N=CHAr     IV

NC—N=C(Ar)NHR¹     V

-continued

NC—N=C(Ar)OCH₃     VI

Cl—N=C(Ar)NHR¹     VII

ArCOOCH(alkyl)C(=O)alkyl     VIII

We claim:

1. A method for the control of arthropod pests at an infected locus which comprises treating said locus with an arthropodicidally effective amount of a 2-phenylimidazole derivative of the formula (I):

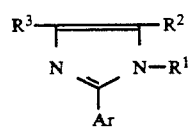

wherein
R¹ represents the hydrogen atom or a straight- or branched-chain alkyl group having from 1 to 6 carbon atoms, which is optionally substituted by a straight- or branched-chain alkoxy, alkylthio, alkylsulphinyl or alkylsulphonyl group having from 1 to 6 carbon atoms, a cyano group, a carboxy group or a straight- or branched-chain alkoxycarbonyl group having from 2 to 7 carbon atoms; R² and R³, which can be the same or different, each represents a hydrogen atom, a halogen atom, a nitro group, a carboxy group, a cyano group, a straight- or branched-chain alkoxycarbonyl or alkanoyl group having from 2 to 7 carbon atoms, a carbamoyl or sulphamoyl group which can be substituted by one or two straight- or branched-chain alkyl groups each having from 1 to 6 carbon atoms, an amino group which can be substituted on the nitrogen atom by one or two substituents selected from the group consisting of straight- and branched-chain alkyl groups having from 1 to 6 carbon atoms and straight- and branched-chain alkoxycarbonyl and alkanoyl groups having 2 to 7 carbon atoms, or represents a group R, RO, RS, RSO or RSO₂ in which R represents a straight- or branched-chain alkyl group having 1 to 6 carbon atoms which is optionally substituted by one or more halogen atoms; and Ar represents a substituted 2,4-disubstituted phenyl group of the formula

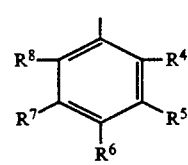

wherein R⁴ and R⁶, which can be the same or different, each represents a halogen atom or a group R, RO, RS, RSO or RSO₂ in which R represents a straight-or branched-chain alkyl group having 1 to 6 carbon atoms which is substituted by one or more halogen atoms;

and R⁵, R⁷ and R⁸, which can be the same or different, each represents a substituent as defined above for R⁴, a hydrogen atom, a hydroxy group, a carboxy group, a nitro group, a cyano group, an amino group, a straight- or branched-chain alkylamino group having from 1 to 6 carbon atoms which can be substituted on the nitrogen atom by a straight- or branched-chain alkyl group having 1 to 6 carbon atoms or by a straight- or branched-chain alkoxycarbonyl or alkanoyl group having 2 to 7 carbon atoms; or an arthropodicidally acceptable salt thereof; with the exclusion of compounds in which $R^2$ and $R^3$ simultaneously represent hydrogen atoms.

2. The method for controlling arthropod pests according to claim 1, wherein said infected locus is a crop growing locus.

3. The method for the control of arthropod pests according to claim 1, wherein said infected locus is selected from the group consisting of forage crops, plantation crops, field crops, glasshouse crops, orchard crops, vineyard crops, grove crops, shrubs, trees, timber and ornamental plants.

4. The method for the control of arthropod pests according to claim 1, wherein said infected locus is selected from the group consisting of cereals, grains, nuts, animal feedstuffs, vegetables, fruits, spices, tobacco and meats.

5. The method for the control of arthropod pests according to claim 1, wherein said infected locus is selected from the group consisting of animal skins, hair, wool, feathers, carpets and textiles.

* * * * *